US008980391B2

(12) United States Patent
Chen et al.

(10) Patent No.: US 8,980,391 B2
(45) Date of Patent: Mar. 17, 2015

(54) VULCANIZATION COMPOSITION HAVING REDUCED ALLERGENIC POTENTIAL, AND ELASTOMERIC ARTICLES FORMED THEREWITH

(75) Inventors: Seong Fong Chen, Penang (MY); Wei Cheong Wong, Kedah (MY); Chii Yih Low, Penang (MY)

(73) Assignee: Allegiance Corporation, McGaw Park, IL (US)

( * ) Notice: Subject to any disclaimer, the term of this patent is extended or adjusted under 35 U.S.C. 154(b) by 200 days.

(21) Appl. No.: 13/169,872

(22) Filed: Jun. 27, 2011

(65) Prior Publication Data
US 2012/0021155 A1 Jan. 26, 2012

Related U.S. Application Data

(60) Provisional application No. 61/358,721, filed on Jun. 25, 2010.

(51) Int. Cl.
| | | |
|---|---|---|
| *B29D 22/00* | (2006.01) | |
| *B29D 23/00* | (2006.01) | |
| *B32B 1/08* | (2006.01) | |
| *C08K 5/00* | (2006.01) | |
| *C08K 3/22* | (2006.01) | |
| *C08K 5/38* | (2006.01) | |
| *A61B 19/04* | (2006.01) | |
| *A61B 19/08* | (2006.01) | |

(52) U.S. Cl.
CPC ............ *C08K 5/0025* (2013.01); *C08K 3/22* (2013.01); *C08K 5/38* (2013.01); *A61B 19/04* (2013.01); *A61B 19/081* (2013.01); *A61B 19/088* (2013.01); *A61B 2019/043* (2013.01)
USPC ........................................................ 428/36.8

(58) Field of Classification Search
USPC ........................................................ 428/36.8
See application file for complete search history.

(56) References Cited

U.S. PATENT DOCUMENTS

| | | | |
|---|---|---|---|
| 3,378,538 A | 4/1968 | Sparks | |
| 3,397,173 A | 8/1968 | Collette et al. | |
| 4,605,705 A | 8/1986 | Takeshita | |
| 4,695,609 A * | 9/1987 | Stevenson | 525/352 |
| 2003/0161975 A1 | 8/2003 | Lucas et al. | |
| 2008/0190322 A1 | 8/2008 | Chen et al. | |

FOREIGN PATENT DOCUMENTS

| | | |
|---|---|---|
| WO | WO 03/072340 A1 | 9/2003 |
| WO | WO 2007/017368 A1 | 2/2007 |
| WO | WO 2008097643 A2 * | 8/2008 |

OTHER PUBLICATIONS

"Guidance for Industry and FDA Reviewers/Staff: Premarket Notification [510(k)] Submissions for Testing Skin Sensitization to Chemicals in Natural Rubber Products," U.S. Department of Health and Human Services (1999).
Chakraborty et al, "Novel Sustainable Accelerators for Latex Applications—Update." *International Rubber Molding Conference* (2005).
Carl, *Neoprene Latex*, chapter 3, published by E.I., du Pont de Nemours & Co. (1962).
Chakraborty et al, "Safer Accelerators for the Latex Industry" (2004), Kuala Lumpur, Malaysia.

* cited by examiner

*Primary Examiner* — Michael C Miggins
(74) *Attorney, Agent, or Firm* — Nada J. Ardeleanu

(57) ABSTRACT

The present invention generally relates to vulcanization compositions used to vulcanize elastomeric articles, where the vulcanization compositions have reduced allergenic potential as compared to elastomeric articles formed using vulcanization compositions having non-fugitive accelerators. The present invention also relates to elastomeric articles formed using the vulcanization compositions. The invention further relates to methods for making a reduced-allergenicity vulcanization composition, and to methods for using the vulcanization compositions to vulcanize elastomeric articles.

16 Claims, No Drawings

VULCANIZATION COMPOSITION HAVING REDUCED ALLERGENIC POTENTIAL, AND ELASTOMERIC ARTICLES FORMED THEREWITH

CROSS-REFERENCE TO RELATED APPLICATIONS

This application claims priority to U.S. Provisional Application No. 61/358,721 titled "Vulcanization Accelerator Composition Having Reduced Allergenic Potential, And Elastomeric Articles Formed Therewith" filed Jun. 25, 2010, the entirety of which is hereby incorporated by reference herein.

BACKGROUND OF THE INVENTION

1. Field of the Invention

The present invention generally relates to vulcanization compositions including accelerator compositions used to vulcanize elastomeric articles, where the vulcanization compositions have reduced allergenic potential as compared to elastomeric articles formed using conventional vulcanization compositions. The present invention also relates to polychloroprene-based elastomeric articles formed using the vulcanization compositions. The invention also relates to methods for making a reduced allergenicity vulcanization composition, and to methods for using the vulcanization compositions to vulcanize elastomeric articles. According to some aspects the vulcanization compositions may include sulfur, the accelerator compositions, and an activator composition. According to another aspect, the accelerator compositions may include a fugitive vulcanization accelerator and the activator composition may include zinc oxide, According to further aspects, the elastomeric articles may include gloves, finger cots, catheters, and condoms.

2. Description of Related Art

There are two types of allergies associated with the use of elastomeric articles in the medical field: (a) Type I immediate hypersensitivity, IgE-mediated allergies; and (b) Type IV delayed hypersensitivity, cell-mediated allergies.

Type I hypersensitivity reactions are mediated by IgE immunoglobulin and the effect is immediate. Generally, symptoms are evident within minutes of exposure to the allergen, and may include local urticaria, facial swelling, watery eyes, rhinitis, asthma, and in extremely rare occasions, anaphylactic shock. Type I allergies have been linked to the residual, extractable proteins present in natural rubber latex products.

Various technologies are available for reducing the extractable proteins in latex gloves, such as water leaching, chlorination, and the use of low-protein or deproteinated latex. However, healthcare personnel and patients who are allergic to natural rubber latex proteins are advised to use synthetic gloves. Commonly-used synthetic materials include polyisoprene, acrylonitrile-butadiene (nitrile), polychloroprene (Neoprene), polyurethane, and polyvinyl chloride.

As a result of the prevalence of Type I reactions in response to contact with natural rubber proteins, there has been a shift towards the use of synthetic latexes that do not contain natural rubber latex proteins, especially for use in making medical devices that come into contact with the skin. Taking cost and performance into consideration, synthetic latexes that are suitable for glove manufacture include nitrile latex and polyurethane latex for examination gloves, and polychloroprene latex and polyisoprene latex for surgical gloves. For surgical gloves, polyisoprene latex has typically been preferred over polychloroprene, even though it is more expensive, because it provides the gloves with properties that mimic those of natural rubber, particularly tensile strength, ultimate elongation, softness and comfortable feel.

However, Type IV allergic reactions can be caused by natural or synthetic elastomeric articles. Synthetic latexes can still cause allergic reactions due to the use of certain chemicals that may be found in the compounded latex. Type IV delayed hypersensitivity reactions are cell-mediated allergic responses to specific chemicals. Symptoms only become apparent about 48-96 hours after contact. Chemicals that may induce Type IV allergic responses include vulcanization accelerators such as thiurams, mercaptobenzothiazoles, dithiocarbamates, diphenylguanidines, and thioureas, which are used in the process of preparing the elastomeric articles. The U.S. Food and Drug Administration (FDA) acknowledges that thiazoles, thiurams, and carbamates in rubber products can induce Type IV allergic reactions in humans. "Guidance for Industry and FDA Reviewers/Staff: Premarket Notification [510(k)] Submissions for Testing for Skin Sensitization to Chemicals in Natural Rubber Products," U.S. Department of Health and Human Services (1999). Hence, it is important to minimize the level of accelerators used so that the residual accelerator in the finished elastomeric article is very low.

Elastomeric articles are generally manufactured using a latex dipping process, which involves dipping molds or formers into a coagulant solution (usually aqueous calcium nitrate). After evaporating off the solvent, the coagulant-coated molds/formers are then dipped into compounded latex such that a film of coagulated rubber particles is deposited thereon. After gelling the latex film using heat, the wet-gelled latex film is leached in water and then dried and vulcanized in a hot air oven. During vulcanization the rubber molecules are chemically crosslinked.

Most commonly, the crosslinking agent is sulfur. However, sulfur alone is inefficient for forming crosslinks. Conventionally, sulfur has always been used in combination with vulcanization accelerators and activators.

Vulcanization accelerators are usually organic compounds that increase the rate and efficiency of sulfur crosslinking, while activators are compounds that increase the efficiency of the accelerators. Examples of accelerators used in latex compounding include thiurams, dithiocarbamates, mercaptobenzthiazole, diphenylguanidine, and thioureas. After vulcanization, depending on the amount of the accelerator used, some or most of the accelerators are chemically bonded to the rubber matrix, but some are unreacted and may remain as a residue in the finished elastomeric article.

Vulcanization activators used in latex compounding are usually metal oxides, such as zinc oxide, magnesium oxide, and lead oxide.

Various methods for minimizing or eliminating Type IV allergic reactions caused by vulcanization accelerators have been attempted, including crosslinking without the use of sulfur and vulcanization accelerators. Approaches include (a) crosslinking using gamma irradiation, (b) crosslinking using organic peroxides, (c) crosslinking using zinc oxide alone, via carboxyl-zinc ionic bonding, and (d) introducing functional groups into the polymer backbone that can form crosslinks after the product has been fabricated. Generally speaking, all of these approaches suffer from drawbacks. For example, approaches (a) and (b) result in products having poorer physical properties and poorer aging resistance than sulfur-vulcanized products.

Another approach is the use of safer accelerators. These are accelerators that have a lower allergenic potential. For example, a high-molecular weight accelerator that has low allergenic potential may be used, including, e.g., zinc dibenzyl dithiocarbamate (ZBEC), and zinc diisononyl dithiocarbamate (ZDNC). By virtue of their high molecular weights, these types of accelerators are more compatible with natural rubber and synthetic polyisoprene rubber, and therefore have a higher solubility in the rubber matrix. As a result, very little of the high-molecular weight accelerator would bloom to the rubber surface and come in contact with the user to cause a potential allergic reaction. For the same reason, very little of the high-molecular weight accelerator can be extracted from the rubber. ZDNC is preferred over ZBEC because it has a higher solubility in natural rubber (about 3% weight/weight), whereas the solubility of ZBEC is only about 0.5% weight/weight.

A further approach is to use combinations of fugitive accelerators, i.e., accelerators that are completely used up during vulcanization, leaving no residue in the product. Examples of such fugitive accelerators include xanthates, such as diisopropyl xanthogen polysulfide (DIXP), or dibutyl xanthogen disulfide (DBXD). Heating DIXP alone to high temperatures does not volatalize or decompose it completely to gaseous products. However, when DIXP is used together with sulfur and zinc oxide for crosslinking a diene containing polymer or rubber, it is consumed completely to form sulfur crosslinks, isopropanol and carbon disulfide as the major reaction products, leaving behind virtually no residue on the polymer or rubber since isopropanol and carbon disulfide would volatilize at the crosslinking/vulcanization temperatures. Since DIXP does not contain nitrogen in its chemical structure, it is also impossible to generate N-nitrosamines, which are associated with thiuram and dithiocarbamate accelerators. Additionally, certain nitrosamines are believed to be carcinogenic, and their formation should be avoided. However, DIXP alone does not accelerate sulfur crosslinking sufficiently to produce enough sulfur crosslinks to yield useful products. The resulting articles have a tensile strength that is too low. Hence, DIXP has always been used in conjunction with another accelerator.

A variety of accelerator compositions have been disclosed in the prior art, some of which are discussed below.

U.S. Published Application No. 2003/0161975 discloses the use of sulfur and DIXP, together with tetrabenzyl thiuram disulfide or ZBEC to produce polyisoprene condoms that are defect-free. The latex compound has improved stability compared to latexes formed using conventional accelerators such as zinc diethyl dithiocarbamate and zinc dibutyl dithiocarbamate.

A synergistic combination of DIXP and ZDNC has been recommended as a safer accelerator for use with natural rubber latex and synthetic polyisoprene latex. Chakraborty et al., "Novel Sustainable Accelerators for Latex Applications—Update," *International Latex Conference* (2005).

For vulcanizing polychloroprene, conventional curing packages include sulfur, non-fugitive accelerators, and zinc oxide. Non-fugitive accelerators that are used include zinc dibutyl dithiocarbamate (ZDBC); a mixture of tetraethylthiuram disulfide and sodium dibutyl dithiocarbamate; and a mixture of diphenyl thiourea (thiocarbanilide) and diphenyl guanidine (see Carl, Neoprene Latex, chapter 3, published by E.I., du Pont de Nemours & Co. (1962)). However, residuals of these non-fugitive accelerators in the product can induce Type IV allergic reactions.

Chakraborty et al. "*Safer Accelerators for the Latex Industry*" (2004), Kuala Lumpur, Malaysia disclosed formulations using sulfur, two combinations of two accelerators (ZDNC and DIXP, or ZDEC and MBT), zinc oxide, and two antioxidants (AO2246 and MMBI).

Jole Van (WO 2007/017368) also disclosed formulations using sulfur, accelerators (DIXP and alkyl dithiocarbamates of various chain lengths, such as ZDNC, and DPG), zinc oxide, and an antioxidant (Aquanox L).

Lucas (WO 2003/072340) disclosed formulations using sulfur, accelerators (various combinations comprising DIXP, DIX, XS, TETD, TBeTD, and ZDBeC), zinc oxide, and an antioxidant (Wingstay L).

Sparks et al. (U.S. Pat. No. 3,378,538) discloses a process for preparing a sulfur-modified polychloroprene by polymerizing in the presence of sulfur and a dialkyl xanthogen disulphide.

Collette et al. (U.S. Pat. No. 3,397,173) discloses a process for polymerizing chloroprene and sulfur in an aqueous emulsion to form a latex. The polymerization is conducted in the presence of sulfur, dialkyl xanthogen disulfide, and an antioxidant.

Takeshita (U.S. Pat. No. 4,605,705) disclose a heat-resistant, sulfur-modified polychloroprene copolymer of 2-chloro-1,3-butadiene and 2,3-dichloro-1,3-butadiene formed using elemental sulfur, and diisopropyl xanthogen disulfide or an equivalent amount of a dialkyl xanthogen disulfide, such as dibutyl xanthogen disulfide.

Accordingly, there is a need in the art for vulcanization compositions used to vulcanize elastomeric articles, where the vulcanization compositions have reduced allergenic potential as compared to elastomeric articles formed using vulcanization compositions having non-fugitive accelerator compositions. The present invention also relates to polychloroprene-based elastomeric articles formed using the vulcanization compositions. The invention also relates to methods for making a reduced allergenicity vulcanization composition, and to methods for using the vulcanization compositions to vulcanize elastomeric articles.

SUMMARY OF THE INVENTION

The present invention provides vulcanization compositions having accelerator compositions that are used to vulcanize elastomeric articles. The vulcanization compositions have reduced allergenic potential as compared to vulcanization compositions having non-fugitive accelerator compositions, and may be used to form elastomeric articles that have reduced allergenic potential as compared to elastomeric articles formed using vulcanization compositions having non-fugitive accelerator compositions. Non-fugitive accelerator compositions may include thiazoles, thiurams, carbamates, guanidines, and thioureas. The present invention also relates to polychloroprene-based elastomeric articles formed using the vulcanization compositions. The invention further relates to methods for making a reduced allergenicity vulcanization composition, and to methods for using the vulcanization compositions to vulcanize elastomeric articles.

The present invention meets the unmet needs of the art, as well as others, by providing vulcanization compositions, latex dispersions, and elastomeric articles that exhibit reduced or eliminated allergic potential as compared to vulcanization compositions, latex dispersions, and elastomeric articles formed using conventional techniques. According to some aspects, the present invention results in reduced or eliminated Type I and Type IV allergenicity. The vulcanization compositions, latex dispersions, elastomeric articles, and methods of the present invention are beneficial for avoiding problems associated with allergic reactions to elastomeric articles, particularly in the medical field, where both health care providers and patients are exposed to these potential sources of allergens frequently and/or for extended periods of time.

According to one aspect of the invention, the invention relates to a vulcanization composition comprising sulfur, a single fugitive xanthate accelerator, and a metal oxide, where the vulcanization composition does not include an additional accelerator. According to another aspect of the invention, the invention relates to a vulcanization composition comprising sulfur, one or more fugitive xanthate accelerators, and a metal oxide, where the composition does not include a non-fugitive accelerator. According to some aspects, the vulcanization composition exhibits reduced allergenicity as compared to vulcanization compositions comprising non-fugitive accelerators.

According to another aspect of the invention, the vulcanization composition comprises sulfur, diisopropyl xanthogen polysulfide, and a metal oxide, and does not include an additional accelerator. According to another aspect of the invention, the vulcanization composition comprises sulfur, diisopropyl xanthogen polysulfide, and a metal oxide, and does not include a non-fugitive accelerator. According to some aspects, the vulcanization composition exhibits reduced allergenicity as compared to vulcanization compositions comprising non-fugitive accelerators.

According to yet another aspect of the invention, the vulcanization composition consists of sulfur, an accelerator composition including diisopropyl xanthogen polysulfide, and an activator including a metal oxide. According to some aspects, the accelerator composition exhibits reduced allergenicity as compared to non-fugitive accelerators.

Still another aspect of the invention provides a latex dispersion comprising an elastomer and a vulcanization composition comprising sulfur, a single fugitive xanthate accelerator, and a metal oxide, where the composition does not include an additional accelerator. Another aspect of invention provides a latex dispersion comprising an elastomer and a vulcanization composition comprising sulfur, one or more fugitive xanthate accelerators, and a metal oxide, where the composition does not include a non-fugitive accelerator. According to some aspects, the elastomeric articles exhibit reduced allergenicity as compared to elastomeric articles formed using non-fugitive accelerators. According to further aspects, the elastomer is polychloroprene. According to still further aspects, the latex formulation may be used to form elastomeric articles that may include, but are not limited to, gloves (specifically medical gloves, and more specifically examination and surgical gloves), as well as condoms, probe covers, dental dams, finger cots, and catheters.

According to further aspects of the invention, a method of preparing a reduced-allergenicity vulcanization composition is provided, in which sulfur, a single fugitive xanthate accelerator, and a metal oxide are combined. The method does not include a step of providing an additional accelerator composition. According to another aspect of the invention, a method of preparing a reduced-allergenicity vulcanization composition is provided, in which sulfur, one or more fugitive xanthate accelerators, and a metal oxide are combined. The method does not include a step of providing a non-fugitive accelerator.

According to still further aspects of the invention, a method of preparing a reduced-allergenicity elastomeric article is provided, in which a latex dispersion is formed that includes vulcanization composition comprising sulfur, a single fugitive xanthate accelerator, and a metal oxide, and the latex dispersion is used to form an elastomeric article. In some aspects, the elastomeric article may be formed by the coagulant dipping method. The method does not include a step of adding another accelerator composition to form the article. According to another aspect of the invention, a method of preparing a reduced-allergenicity elastomeric article is provided, in which a latex dispersion is formed that includes a vulcanization composition comprising sulfur, one or more fugitive xanthate accelerators, and a metal oxide, and the latex dispersion is used to form an elastomeric article. The method does not include a step of adding a non-fugitive composition to form the article.

Other novel features and advantages of the present invention will become apparent to those skilled in the art upon examination of the following or upon learning by practice of the invention.

DETAILED DESCRIPTION OF THE PREFERRED EMBODIMENTS

The present invention generally relates to vulcanization compositions including accelerator compositions used to vulcanize elastomeric articles, where the accelerator compositions have reduced allergenic potential as compared to elastomeric articles formed using vulcanization compositions having non-fugitive accelerator compositions. The vulcanization compositions comprise sulfur, zinc oxide, and a fugitive vulcanization accelerator. The present invention also relates to latex dispersions and elastomeric articles formed using the vulcanization compositions. The present invention further relates to methods for making a reduced allergenicity vulcanization composition, and to methods for using the vulcanization compositions to vulcanize elastomeric articles.

Fugitive vulcanization accelerators for use in accordance with the present invention include xanthates. Diisopropyl xanthogen polysulfide (DIXP) and dialkyl xanthogen disulfides are preferred fugitive xanthates that may be used in accordance with the present invention, and it is envisioned that additional fugitive xanthates that may be developed in the future will also find use in the accelerator compositions, latex dispersions, and elastomeric articles of the present invention. Fugitive xanthates are useful in the accelerator compositions of the vulcanization compositions of the present invention because during vulcanization they are consumed by bonding to the rubber matrix, and form gases and/or volatile liquids as by-products that evaporate, thereby leaving no residue on the elastomeric article. In the case of diisopropyl xanthogen polysulfide (DIXP), the compound form isopropyl alcohol and carbon disulfide gas as by-products.

The present invention also provides elastomeric articles made from polychloroprene rubber and vulcanized using sulfur, zinc oxide, and DIXP. According to some aspects, the elastomeric articles may include gloves (specifically medical gloves, and more specifically examination and surgical gloves), as well as condoms, probe covers, dental dams, finger cots, and catheters. According to certain aspects polychloroprene surgical and examination gloves made using such an accelerator composition are provided.

Elastomeric articles made using non-fugitive accelerator compositions contain residual accelerators that could cause Type IV allergy reactions in humans, and elastomeric articles made using natural rubber contain extractable latex proteins that are linked to Type I allergy reactions in humans. Because the elastomeric articles, accelerator compositions, latex compositions, methods of making accelerator compositions, and methods of vulcanizing elastomeric articles in accordance with the present invention do not incorporate natural rubber, and do not have residual accelerators included therein, the potential for Type I allergic reactions and Type IV allergic reactions is reduced or eliminated. Non-fugitive accelerator compositions may include thiazoles, thiurams, carbamates, and the like, which are known to cause Type IV allergy reactions in humans. Other non-fugitive accelerators such as guanidines and thioureas have also been used in rubber gloves.

The compositions and methods of the invention will be described in greater detail below.

Vulcanization Compositions

The vulcanization compositions of the present invention preferably include a source of sulfur, an accelerator composition, and an activator. The accelerator compositions may include a fugitive accelerator. According to certain aspects of the invention, in which the allergenicity of the vulcanization composition is being minimized or eliminated, elemental sulfur and a single xanthate fugitive accelerator are used. In another aspect elemental sulfur and one or more xanthate fugitive accelerators are used and a non-fugitive accelerator is not included. The accelerator is in a range from about 0.1 to about 10 parts by dry weight rubber, preferably from about 0.5 to about 5 parts by dry weight rubber, and more preferably about 1 to about 4 parts by dry weight rubber. The vulcanization compositions may be used to vulcanize elastomers including natural rubber, polyurethane, polybutadiene, polychloroprene (Neoprene), nitrile rubber, block copolymers of styrene and butadiene, block copolymers of styrene and isoprene, and polyisoprene. In certain preferred aspects of the invention, the elastomer is polychloroprene.

In aspects of the invention in which the allergenicity of the vulcanization composition is being minimized or eliminated altogether, the source of sulfur used in the vulcanization composition comprises elemental sulfur. According to certain aspects of the invention, only elemental sulfur is used.

The vulcanization activator may include, but is not limited to, zinc oxide, magnesium oxide, lead oxide, and combinations thereof. Zinc oxide is used as a vulcanization activator in certain aspects of the invention. The activator is in a range from about 0.1 to about 15 parts by dry weight rubber, preferably from about 6 to about 12 parts by dry weight rubber, and more preferably from about 5 to about 13 parts by dry weight rubber.

In aspects of the invention in which the allergenicity of the vulcanization composition is being minimized or eliminated altogether, the vulcanization accelerator used in accordance with aspects of the invention is a fugitive xanthate. According to some aspects, the fugitive xanthate is a polysulfide that includes more than two sulfide groups, i.e., three or more sulfide groups (trisulfide), four or more sulfide groups (tetrasulfide), five or more sulfide groups (pentasulfide), etc. According to further aspects of the invention, the fugitive xanthate is diisopropyl xanthogen polysulfide (DIXP) or a dialkyl xanthogen disulfide, such as dibutyl xanthogen disulfide, and diisopropyl xanthogen disulfide. It should be noted that these fugitive xanthate accelerators can also serve as sulfur donors. In an aspect of the invention, the sulfur donor has a low allergenic potential. The elemental sulfur or sulfur donor is in a range from about 0.1 to about 5 parts by dry weight rubber, preferably from about 0.5 to about 2 parts by dry weight rubber, and more preferably from about 1.2 to 1.5 parts by dry weight rubber.

In certain aspects of the invention, only a single fugitive xanthate vulcanization accelerator is used in the accelerator composition, and any additional vulcanization accelerators are excluded from the accelerator composition. In another aspect one or more fugitive xanthate accelerators may be used, and a non-fugitive accelerator is not used.

According to further aspects of the invention, DIXP is used as the sole vulcanization accelerator, and is the only compound that functions as a vulcanization accelerator that is included in the accelerator composition. When accelerator compositions having reduced or eliminated allergenicity are prepared in accordance with the present invention, they may beneficially comprise only DIXP as a fugitive accelerator. Any additional compounds that may also function as vulcanization accelerators are excluded from the accelerator compositions. In another aspect, additional fugitive accelerators may be included in the accelerator compositions, but additional non-fugitive accelerators are excluded. The exclusions in either aspect are beneficial because the presence of any additional vulcanization accelerators or the use of non-fugitive accelerators increases the likelihood that an allergic reaction, particularly a Type IV allergic reaction, may occur in a user of an elastomeric article formed with the vulcanization composition.

Latex Dispersions and Elastomeric Articles

The vulcanization compositions of the present invention may be used to prepare latex dispersions. The latex dispersion may comprise an elastomer that may be selected from natural rubber, polyurethane, polybutadiene, polychloroprene (Neoprene), nitrile rubber, block copolymers of styrene and butadiene, block copolymers of styrene and isoprene, and polyisoprene. According to certain aspects, a particularly preferred elastomer for use in the latex dispersions of the invention is polychloroprene. These latex dispersions may comprise, in addition to the elastomer and vulcanization composition, one or more different non-curing ingredients. The non-curing ingredients may include, but are not limited to, antioxidants, stabilizers, plasticizers, anti-ozone agents, pigments, and fillers. According to an aspect of the invention, when making the first elastomeric layer (base glove), the total solids content of the latex dispersion is in a range from about 20% to about 45%. According to some aspects of the invention for preparing a coating composition suitable for forming a second, third, fourth, etc. elastomeric layer (e.g., as described in U.S. Published Appl. No. 2008/0190322 A1, which is incorporated herein by reference in its entirety), the total solids content of the latex dispersion is adjusted so that it is in a range of from about 1% to about 20%, preferably from about 2% to about 17%, and more preferably from about 3% to about 15%. According to one aspect of the invention, the total solids content of the latex dispersion is about 5%. According to other aspects of the invention for preparing a single layer glove, or the first elastomeric layer of a glove having two or more layers, the total solids content of the latex dispersion is generally in the range of from about 20% to about 45%, preferably from about 25% to about 40%.

The latex dispersions of the present invention that contain an elastomer and vulcanization composition may be used in methods for preparing elastomeric articles such as gloves, specifically medical gloves, and more specifically examination and surgical gloves. However, it is considered within the ability of those skilled in the art to prepare alternative elastomeric articles other than gloves, including, but not limited to, condoms, probe covers, dental dams, finger cots, catheters, and the like, using the guidance provided herein.

The elastomeric articles of the present invention that are formed using the vulcanization compositions and/or latex dispersions described above may be produced using any conventional manufacturing methods, e.g., coagulant dipping. In the "anode" coagulant-dipping process, a coagulant-coated former is dipped into the dispersion, and is then cured to form a finished article. In the "Teague" coagulant-dipping process, the former is dipped into the dispersion, and is then dipped into a coagulant, followed by curing to form a finished article. These methods utilize dispersions containing the elastomer from which the finished article is to be formed. Preferred elastomers include natural rubber, polyurethane, polybutadiene, polychloroprene (Neoprene), nitrile rubber, block copolymers of styrene and butadiene, block copolymers of styrene and isoprene, and polyisoprene. According to certain aspects, a particularly preferred elastomer is polychloroprene. According to still further aspects, a polychloroprene elastomeric article is provided that is vulcanized using an vulcanization composition consisting of sulfur, zinc oxide, and DIXP.

In prior art compositions, DIXP has always been used in combination with additional accelerators including non-fugitive accelerators, because it is not sufficiently active on its own to form adequate numbers of sulfur crosslinks to form a useful elastomeric article. However, the present invention has unexpectedly discovered that it is possible to vulcanize polychloroprene latex with a vulcanization composition consisting of sulfur, DIXP, and zinc oxide in order to obtain an elastomeric article having a tensile strength that meets the ASTM D6977-04 requirements for polychloroprene examination gloves (minimum 14 MPa), as well as the ASTM D3577-01 requirements for synthetic latex surgical gloves (minimum 17 MPa). Because DIXP is a fugitive xanthate, and no DIXP residue remains on the gloves following vulcanization, the gloves produced using this vulcanization composition exhibit low allergenic potential.

Polychloroprene rubber can form crosslinks between polymer chains in the presence of a catalyst, such as zinc oxide, magnesium oxide, or lead oxide, unlike natural rubber or synthetic polyisoprene rubber. Without wishing to be bound by theory, this crosslinking is believed to occur as a result of a bis-alkylation mechanism that is specific to polychloroprene due to its chemical structure. The crosslinking between polymer chains is believed to take place at sites on the polymer chain where there are reactive tertiary allylic chlorine atoms formed by 1,2-polymerization of chloroprene monomers. The labile chlorine amounts to about 1.5% of the total chlorine in the polychloroprene polymers. In addition to this type of crosslinking, it is also possible that sulfur crosslinking could occur at other sites on the polymer chain. See Carl, *Neoprene Latex*, chapter 3.

The elastomeric articles of the present invention may be formed using latex dispersions containing any additives components that may be used in forming the elastomeric articles, which may include at least one of curing ingredients, non-curing ingredients, and additional polymers, to be discussed below, with the same, similar or different chemical structures from the elastomer. The total amount of additive(s) used is about 0.5-49% by weight of total dispersion phase solids.

When curing using sulfur, the main curing agent preferably comprises elemental sulfur and/or a sulfur donor that has low or no allergenic potential. According to certain aspects of the invention, only elemental sulfur is used.

Activators may include, but are not limited to, zinc oxide, magnesium oxide, and lead oxide. Zinc oxide is the most commonly used vulcanization activator.

Vulcanization accelerators in accordance with the invention are fugitive xanthates. According to further aspects of the invention, the fugitive xanthate is diisopropyl xanthogen polysulfide (DIXP) or a dialkyl xanthogen disulfide, such as dibutyl xanthogen disulfide, and diisopropyl xanthogen disulfide.

Any non-curing ingredients that are conventionally used in elastomer dispersion compounding formulations may be used in the present invention. For example, the non-curing ingredients may include, but are not limited to, antioxidants, stabilizers, plasticizers, anti-ozone agents, pigments, and fillers.

Suitable antioxidants that may be added to the elastomer dispersion include, but are not limited to, hindered phenols such as butylated hydroxytoluene (2,6-di-tert-butyl-4-methylphenol) and thiodiethylene bis-di-t-butyl-4-hydroxyphenyl propionate, hindered polyphenolics such as butylated reaction products of p-cresol and dicyclopentadiene, hindered phenol/hindered polyphenolics such as trimethyl-tris (di-t-butyl-4-hydroxybenzym)-benzene or octadecyl di-t-butyl-4-hydroxyphenyl propionate, amines such as a blend of 6PPD with methyl styrene and bis-alpha-dimethylbenzyl diphenyl amine, mixtures such as zinc mercaptotulumimidazole/phenolic, triazinone derivatives such as triazinone-phenol mixtures, polyaromatic amines such as poly(m-anisidine), phenolic antioxidant hydrazides such as phenolics with anhydride copolymer, phenolics such as 2,2'-methylene-bis-(4-methyl-6-t-butylphenol), cresols such as 2,4-dimethyl-6-(1-methylcyclohexyl)-p-cresol, and styrenated phenols. One particularly preferred antioxidant is butylated reaction products of p-cresol and dicyclopentadiene (e.g., Wingstay L).

Colloidal stabilizers including alkalis for pH adjustment, surfactants and alkaline caseinates such as sodium caseinate may also be added to the aqueous phase.

Suitable plasticizers that may be added to the elastomer dispersion may include, but are not limited to, fatty salts, mineral oils and ester plasticizers.

According to some aspects, an antiozonant is added to an elastomer dispersion that is used to make the elastomeric articles of the invention. Ozone can severely damage some elastomeric articles, such as those formed from polymers that are highly unsaturated, like polyisoprene. When included in the aqueous elastomer dispersion of the invention, certain high molecular weight polymers, such as waxes, EPDM and hydrogenated polydiene can provide such articles with excellent ozone resistance. Waxes form a physical barrier at the surface of the rubber which protects against ozone attack. There are two types of waxes: straight chain paraffin waxes and branched-chain microcrystalline waxes. The most widely used antiozonant waxes are blends of paraffin and microcrystalline waxes for maximum protection over a broad range of exposure temperatures. Paraffin waxes are straight-chain hydrocarbon molecules containing about 20 to 50 carbon atoms. Suitable paraffin waxes have a melting point of from about 50 to 75° C., preferably 52 to 68° C. Microcrystalline waxes are also known as amorphous waxes and are hydrocarbons, similar to paraffin waxes, but the carbon chains are branched and have higher molecular weight of about 40 to 70 carbon atoms per chain. Other examples of antiozonants that may be used in the invention may include, but are not limited to, alkyl/aryl p-phenylenediamines such as N-1,3-dimethyl-butyl-N'-phenyl-p-phenylenediamine 6PPD, organoclay-antiozonant complexes such as smectite-containing clay with alkyl-aryl-p-phenylenediamine, functionalized benzotriazoles such as N,N-disubstituted para-phenylenediamine, triazines such as tris (N-1,4-dimethylpentyl-p-phenylenediamino) 1,3,5-triazine and tris (N-alkyl-p-phenylenediamino) 1,3,5-triazine, and p-phenylenediamines such as N-isopropyl-N'-phenyl-p-phenylenediamine (IPPD). In addition, polymers including waxes such as paraffinic wax (MW=300-500), microcrystalline wax (MW=600-700) (with paraffinic wax) and low MW PE wax (MW=100-1100), polymeric antiozonants such as polymeric diphenyldiamine, and ozone inert polymers such as EPDM and brominated isobutylene/para-methylstyrene copolymer (BIMSM) may be used as antiozonants. It is preferred that waxes are used. Once particularly preferred wax is Michem Lube 180. Another preferred wax dispersion is Antilux 600.

Suitable pigments that may be added to the aqueous elastomer dispersion may include a wide range of natural pigments such as titanium dioxide and iron oxides, and synthetic pigments.

Suitable fillers that may be added to the aqueous elastomer dispersion may include, but are not limited to, inorganic fillers such as clays, calcium carbonate, talc, and silica and organic fillers such as crosslinked polymethyl methacrylate, finely divided urethane resin particles and polyethylene microspheres.

Additional polymers may also be incorporated into the latex dispersions and elastomeric articles of the present invention. This may be done to provide additional functionality or impart beneficial properties to the latex dispersions and elastomeric articles. Such functions/properties may include, but are not limited to, improved damp/wet donning, improved fluid repellency, improved resistance to microorganisms, improved resistance to degradation, etc. According to some aspects of the invention, the additional polymer is selected from natural rubber, polyurethane, polybutadiene, polychloroprene (Neoprene), nitrile rubber, block copolymers of styrene and butadiene, block copolymers of styrene and isoprene, and polyisoprene. When present, the additional polymer may be provided in an amount that is from about 5% to about 200% of the primary polymer, preferably from about 25% to about 150%, more preferably from about 50% to about 125%, and still more preferably from about 75% to about 100%. One exemplary latex dispersion containing additional polymers includes 2.5% polychloroprene, 2.5% synthetic polyisoprene, and 95% water (i.e., the additional polymer, polyisoprene, is provided in an amount that is 100% of the amount of the primary polymer, polychloroprene). Another exemplary latex dispersion containing additional polymers includes 2.5% polychloroprene, 2.5% nitrile, and 95% water.

According to some aspects of the invention, elastomeric articles are provided that include multiple elastomeric layers, where the multiple elastomeric layers may have the same or different compositions. For example, a coating comprising synthetic polyisoprene blended with polychloroprene may be applied to a polychloroprene elastomeric article to provide improved damp/wet donning characteristics to the article. In another example, a coating composition comprising nitrile blended with polychloroprene may be applied to a polychloroprene elastomeric article to provide improved damp/wet donning characteristics to the article.

According to further aspects of the invention, the elastomeric articles may be formed either with, or without, powder or starch. Although powder and starch are commonly-used donning agents, they could be also associated with allergic reactions, and therefore another aspect of the invention relates to powder-free and starch-free elastomeric articles. Further aspects relate to substantially power-free and starch-free elastomeric articles in which less than 5 mg of powder or starch, preferably less than 3 mg of powder or starch, more preferably less than 2 mg of power or starch, and most preferably less than 1 mg of powder or starch. These articles are prepared using the vulcanization compositions described above.

These and other aspects of the invention are further described in the non-limiting Examples set forth below.

EXAMPLES

Example 1

Commercial Powder-Free Polychloroprene Gloves

A commercially available powder-free polychloroprene surgical glove (Duraprene SMT by Cardinal Health) is formed using a vulcanization composition comprising sulfer, zinc dibutyl dithiocarbamate, and zinc oxide. The unaged and aged properties of the gloves are shown in Table 1.

TABLE 1

Physical Properties of Powder-Free Duraprene SMT Gloves

| Properties | Unaged | Aged (7 days, 70° C.) |
|---|---|---|
| Tensile Strength, MPa | 19.6 | 19.1 |
| Tensile Stress @ 500%, MPa | 1.86 | — |
| Ultimate Elongation, % | 1003 | 888 |

Example 2

Preparation of Powdered Gloves

Polychloroprene latex was compounded using a formulation comprising either Formulation A (comparative formulation), which includes only zinc oxide as curing agent, or Formulation B, which includes a combination of sulfur, zinc oxide, and DIXP as curing agent. The complete compounding formulations are set forth in Table 2.

TABLE 2

Compounding Formulations

| Ingredient | Parts per weight dry rubber (phr) Formulation A | Parts per weight dry rubber (phr) Formulation B |
|---|---|---|
| Neoprene 750 Latex | 100.00 | 100.00 |
| Darvan SMO Solution | 4.50 | 4.50 |
| Darvan WAQ Solution | 1.50 | 1.50 |
| Uniflo 26 Solution | 0.50 | 0.50 |
| Zinc Oxide Dispersion | 12.00 | 12.00 |
| Sulfur Dispersion | 0.00 | 1.50 |
| Robac AS100 (DIXP) | 0.00 | 2.00 |
| Wingstay L | 0.75 | 0.75 |
| Michemlube 180 | 1.00 | 1.00 |
| Rodo # 0 | 0.028 | 0.028 |
| Triton X-100 | 0.013 | 0.013 |
| Titanium Dioxide Dispersion | 0.200 | 0.200 |
| Pigment | 0.080 | 0.080 |

Gloves were formed by the standard coagulant dipping process, and were vulcanized using hot air. The properties of the gloves are shown in Table 3.

TABLE 3

Physical Properties of Polychloroprene Gloves

| Properties | Formulation A | Formulation B |
|---|---|---|
| Tensile Strength, MPa | 12.00 | 23.00 |
| Tensile Stress @ 300%, MPa | 0.88 | 1.47 |
| Tensile Stress @ 500%, MPa | 1.08 | 2.55 |
| Ultimate Elongation, % | 1160 | 904 |

The gloves cured only with zinc oxide exhibited a tensile strength of 12 MPa, which was not sufficient to meet ASTM requirements for either examination or surgical gloves. However, the inventive gloves cured with a combination of sulfur, zinc oxide, and DIXP exhibited a tensile strength of 23 MPa, which exceeded the ASTM requirements for polychloroprene examination gloves and surgical gloves made from synthetic latex.

Example 3

Preparation of Powder-Free Gloves

Powder-free polychloroprene gloves were prepared by forming a base glove layer using the standard coagulant dipping process, and using the compounded latex of Formulation B or the compounded latex of Formulation C. The latex formulations are set forth below in Table 4.

TABLE 4

Compounding Formulation

| Ingredient | Parts per weight dry rubber (phr) Formulation B | Parts per weight dry rubber (phr) Formulation C |
|---|---|---|
| Neoprene 750 Latex | 100.00 | 100.00 |
| Darvan SMO Solution | 4.50 | 4.50 |
| Darvan WAQ Solution | 1.50 | 1.50 |
| Uniflo 26 Solution | 0.50 | 0.50 |
| Zinc Oxide Dispersion | 12.00 | 6.00 |
| Sulfur Dispersion | 1.50 | 1.20 |
| Robac AS100 (DIXP) | 2.00 | 3.00 |
| Wingstay L | 0.75 | 0.75 |
| Michemlube 180 | 1.00 | 1.00 |
| Rodo #0 | 0.028 | 0.028 |
| Triton X-100 | 0.013 | 0.013 |
| Titanium Dioxide Dispersion | 0.200 | 0.200 |
| Pigment | 0.080 | 0.080 |

The former bearing the wet base glove layer was then leached in water, and after partial drying was dipped into a blend of compounded polychloroprene latex and nitrile latex so as to form a thin coating of the latex blend onto the base glove layer. The rubber latex blend comprised about 2.5% compounded polychloroprene latex and 2.5% nitrile latex, and about 95% water. Formulations B and C were used as the formulation for the blend of compounded polychloroprene latex with nitrile latex. For example, if Formulation B compounded polychloroprene latex is used for dipping the base polychloroprene glove, then a coating composition having 5% total solids content would contain a blend of 2.5% Formulation B compounded polychloroprene latex and 2.5% raw nitrile latex. Similarly, if Formulation C compounded polychloroprene latex is used for dipping the base polychloroprene glove, then a coating composition having 5% total solids content, the coating composition would contain, for example, a blend of 2.5% Formulation C compounded polychloroprene latex and 2.5% raw nitrile latex. While generally it is convenient for the coating composition to use a blend of raw nitrile latex and compounded polychloroprene latex using the same compounding formulation as that used for the polychloroprene latex for making the base glove, it is possible that the compounding formulations for the base glove and the coating layer be different. For example, it is possible to use Formulation C for making the base glove and Formulation B to blend with raw nitrile latex for coating the base glove.

The former was withdrawn from the latex blend, dried, and then vulcanized in a hot air oven at temperatures of from about 120° C. to about 155° C. After vulcanization, the glove was stripped from the former so that the coated surface was on the inside of the glove. The glove was then turned inside-out so that the coated surface was on the outside of the glove, and was post-processed by chlorination. The chlorination consisted of prewashing the glove with water before chlorination in an aqueous chlorine solution containing about 300 ppm available chlorine, neutralizing any excess chlorine with sodium hydroxide solution, followed by further washing with water (this step was carried out several times). The glove was then partially dried and then manually inverted again and dried further.

For good donning with wet or damp hands, the gloves were transferred to a tumbling washer for a further lubrication process following the chlorination step. This lubrication process included tumbling the gloves with an aqueous solution comprising about 1.0% cetylpyridium chloride, 1.0% silicone emulsion, and 1.5% ammonium salts of alkyl phosphates. The glove was removed from the tumbler washer, partially dried, and manually inverted. The glove was then dried further. The treated glove could be easily donned by dry or damp hands.

The properties of the coated powder-free gloves of Formulations B and C are set forth in Tables 5 and 6.

TABLE 5

Physical Properties of Coated Powder-Free Polychloroprene Gloves Formulation B

| Properties | Unaged | *Aged |
|---|---|---|
| Maturation = 1 day | | |
| Tensile Strength, MPa | 24.0 | 27.6 |
| Tensile Stress @ 300%, MPa | 1.47 | 1.76 |
| Tensile Stress @ 500%, MPa | 2.25 | 2.84 |
| Ultimate Elongation, % | 1002 | 924 |
| Maturation = 3 days | | |
| Tensile Strength, MPa | 23.8 | 27.2 |
| Tensile Stress @ 300%, MPa | 1.37 | 1.76 |
| Tensile Stress @ 500%, MPa | 2.16 | 2.94 |
| Ultimate Elongation, % | 1111 | 865 |
| Maturation = 5 days | | |
| Tensile Strength, MPa | 22.5 | 24.5 |
| Tensile Stress @ 300%, MPa | 1.27 | 1.27 |
| Tensile Stress @ 500%, MPa | 1.96 | 2.45 |
| Ultimate Elongation, % | 1120 | 884 |

*Aging conditions were 7 days at 70° C.

TABLE 6

Physical Properties of Coated Powder-Free Polychloroprene Gloves Formulation C

| Properties | Unaged | *Aged |
|---|---|---|
| Maturation = 2 days | | |
| Tensile Strength, MPa | 17.8 | 19.2 |
| Tensile Stress @ 300%, MPa | 0.98 | 1.37 |
| Tensile Stress @ 500%, MPa | 1.37 | 2.06 |
| Ultimate Elongation, % | 1120 | 924 |
| Maturation = 3 days | | |
| Tensile Strength, MPa | 21.6 | 21.4 |
| Tensile Stress @ 300%, MPa | 1.28 | 1.47 |
| Tensile Stress @ 500%, MPa | 1.86 | 2.84 |
| Ultimate Elongation, % | 963 | 924 |

*Aging conditions were 7 days at 70° C.

It was seen that the coated powder-free gloves of Formulation B had good physical properties both before aging and after accelerated aging for 7 days at 70° C. The tensile strength values for the unaged gloves of Formulation B made from latex that was matured for 1, 3, or 5 days were all greater than 22 MPa, and after accelerated aging, the tensile strength values were all greater than 24 MPa. These values exceeded the ASTM requirements for polychloroprene examination gloves and surgical gloves made from synthetic latex.

The tensile strength values for the unaged coated powder-free gloves of Formulation C made from latex that was matured for 2 or 3 days were approximately the same as the commercial powder free gloves of Example 1. Therefore, the results of shown in Tables 5 and 6 demonstrate that the vulcanization composition can be varied to yield gloves that can meet ASTM requirements for surgical gloves and examination gloves.

Example 4

Preparation of Powder-Free Gloves

Powder-free coated polychloroprene gloves were prepared as described above in Example 3, with the exception that the latex blend used for coating comprised about 2.5% compounded polychloroprene latex, about 2.5% synthetic polyisoprene latex, and about 95% water.

The properties of the resulting gloves were similar to those of the gloves prepared in Example 3.

Example 5

Residual DIXP

Powdered polychloroprene gloves and powder-free polychloroprene gloves were prepared using Formulation B as described in Example 2 and Example 3 (but without the lubrication process). The gloves were tested for residual DIXP using UV spectroscopy. The gloves were extracted with hexane as well as acetonitrile and UV spectra of the extracts were obtained. The UV spectra of both the extracts showed that there was no residual DIXP remaining in either of the powdered or powder-free gloves. The UV spectroscopy testing method has detection limit of 1 ppm.

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application, in order to more fully describe the state of the art to which this invention pertains.

The invention is capable of considerable modification, alteration, and equivalents in form and function, as will occur to those ordinarily skilled in the pertinent arts having the benefit of this disclosure.

While the present invention has been described for what are presently considered the preferred embodiments, the invention is not so limited. To the contrary, the invention is intended to cover various modifications and equivalent arrangements included within the spirit and scope of the detailed description provided above.

We claim:

1. A latex dispersion comprising:
polychloroprene, and a vulcanization composition consisting of:
elemental sulfur, diisopropyl xanthogen polysulfide, and a metal oxide, where the latex dispersion does not include any additional compounds that function as accelerators for vulcanizing elastomers and does not include additional xanthate compounds.

2. An elastomeric article formed using the latex dispersion of claim 1, where the elastomeric article does not include any additional compounds that function as accelerators for vulcanizing elastomers, does not include any additional xanthate compounds, and the elastomeric article has less than 1 ppm residual diisopropyl xanthogen polysulfide.

3. A coating composition for an elastomeric article, comprising: the polychloroprene latex dispersion of claim 1; a second polymer latex selected from the group consisting of natural rubber, polyurethane, polybutadiene, polychloroprene, nitrile rubber, block copolymers of styrene and butadiene, block copolymers of styrene and isoprene, and synthetic polyisoprene; and water, wherein the total solids content of the coating composition is from about 3% to about 15%.

4. The latex dispersion of claim 1, wherein the metal oxide is selected from the group consisting of zinc oxide, magnesium oxide, lead oxide, and combinations thereof.

5. An elastomeric article formed using the coating composition of claim 3, where the elastomeric article does not include any additional compounds that function as accelerators for vulcanizing elastomers and does not include any additional xanthate compounds.

6. The coating composition of claim 3, wherein the second polymer latex is selected from the group consisting of nitrile rubber and synthetic polyisoprene.

7. A latex dispersion comprising:
polychloroprene, and a vulcanization composition consisting of:
elemental sulfur, diisopropyl xanthogen polysulfide, and a metal oxide, where the latex dispersion does not include any non-fugitive accelerators and does not include additional xanthate compounds.

8. An elastomeric article formed using the latex dispersion of claim 7, where the elastomeric article does not include any non-fugitive accelerators, does not include any additional xanthate compounds, and the elastomeric article has less than 1 ppm residual diisopropyl xanthogen polysulfide.

9. The latex dispersion of claim 7, wherein the metal oxide is selected from the group consisting of zinc oxide, magnesium oxide, lead oxide, and combinations thereof.

10. A coating composition for an elastomeric article, comprising: the polychloroprene latex dispersion of claim 7; a second polymer latex selected from the group consisting of natural rubber, polyurethane, polybutadiene, polychloroprene, nitrile rubber, block copolymers of styrene and butadiene, block copolymers of styrene and isoprene, and synthetic polyisoprene; and water, wherein the total solids content of the coating composition is from about 3% to about 15%.

11. The coating composition of claim 10, wherein the second polymer latex is selected from the group consisting of nitrile rubber and synthetic polyisoprene.

12. An elastomeric article formed using the coating composition of claim 10, where the elastomeric article does not include any non-fugitive accelerators and does not include any additional xanthate compounds.

13. A latex dispersion comprising:
polychloroprene, and a vulcanization composition consisting of:
a source of sulfur, a single fugitive xanthate accelerator, and a metal oxide, where the latex dispersion does not include any additional compounds that function as accelerators for vulcanizing elastomers and does not include additional xanthate compounds.

14. The latex dispersion of claim 13, wherein the single fugitive xanthate accelerator is selected from the group consisting of diisopropyl xanthogen polysulfide, dibutyl xanthogen disulfide, and diisopropyl xanthogen disulfide.

15. The latex dispersion of claim 13, wherein the source of sulfur is selected from the group consisting of elemental sulfur and sulfur donors that have a low allergenic potential, and combinations thereof.

16. The latex dispersion of claim 13, wherein the metal oxide is selected from the group consisting of zinc oxide, magnesium oxide, lead oxide, and combinations thereof.

* * * * *